US009804577B1

(12) United States Patent
Troy et al.

(10) Patent No.: US 9,804,577 B1
(45) Date of Patent: Oct. 31, 2017

(54) REMOTELY OPERATED MOBILE STAND-OFF MEASUREMENT AND INSPECTION SYSTEM

(71) Applicant: The Boeing Company, Chicago, IL (US)

(72) Inventors: James J. Troy, Issaquah, WA (US); Scott W. Lea, Renton, WA (US); Gary E. Georgeson, Tacoma, WA (US); William P. Motzer, Seattle, WA (US)

(73) Assignee: The Boeing Company, Chicago, IL (US)

( * ) Notice: Subject to any disclaimer, the term of this patent is extended or adjusted under 35 U.S.C. 154(b) by 864 days.

(21) Appl. No.: 13/892,336

(22) Filed: May 13, 2013

Related U.S. Application Data

(63) Continuation-in-part of application No. 13/166,613, filed on Jun. 22, 2011, and a continuation-in-part of application No. 12/897,408, filed on Oct. 4, 2010, now Pat. No. 8,744,133.

(51) Int. Cl.
*H04N 13/02* (2006.01)
*G05B 15/02* (2006.01)
*H04N 7/18* (2006.01)

(52) U.S. Cl.
CPC ............. *G05B 15/02* (2013.01); *H04N 7/185* (2013.01)

(58) Field of Classification Search
None
See application file for complete search history.

(56) References Cited

U.S. PATENT DOCUMENTS

| 6,658,325 | B2* | 12/2003 | Zweig | B25J 9/1689 318/568.1 |
| 7,859,655 | B2 | 12/2010 | Troy et al. | |
| 8,044,991 | B2 | 10/2011 | Lea et al. | |
| 8,255,170 | B2 | 8/2012 | Kollgaard et al. | |
| 2002/0096844 | A1* | 7/2002 | Clegg | A45C 5/14 280/47.17 |
| 2004/0001750 | A1* | 1/2004 | Kremerman | B25J 9/042 414/744.1 |
| 2007/0076096 | A1* | 4/2007 | Alexander | G06T 7/0018 348/169 |
| 2007/0206115 | A1* | 9/2007 | Kuo | F16M 11/32 348/373 |
| 2008/0307886 | A1* | 12/2008 | Marsh | G01N 29/223 73/601 |
| 2009/0086199 | A1* | 4/2009 | Troy | G01C 1/04 356/251 |
| 2012/0221625 | A1 | 8/2012 | Troy et al. | |

\* cited by examiner

*Primary Examiner* — Frederick Bailey
(74) *Attorney, Agent, or Firm* — Ostranger Chong Flaherty & Broitman P.C.

(57) ABSTRACT

A self-contained, remotely operated, mobile measurement system for stand-off inspection of large target objects located at sites distant from an operations center of a distributed inspection system. In accordance with one embodiment, the system comprises a mobile platform with on-board instrumentation capable of making dimensional measurements in the local coordinate system of the target object. The system comprises multiple hardware and software components networked to a control interface that enables the operator at the operations center to teleoperate the equipment, including driving the mobile platform to a region of interest, calibrating the on-board local positioning system, acquiring measurement and image data, and communicating with on-site personnel if needed.

20 Claims, 11 Drawing Sheets

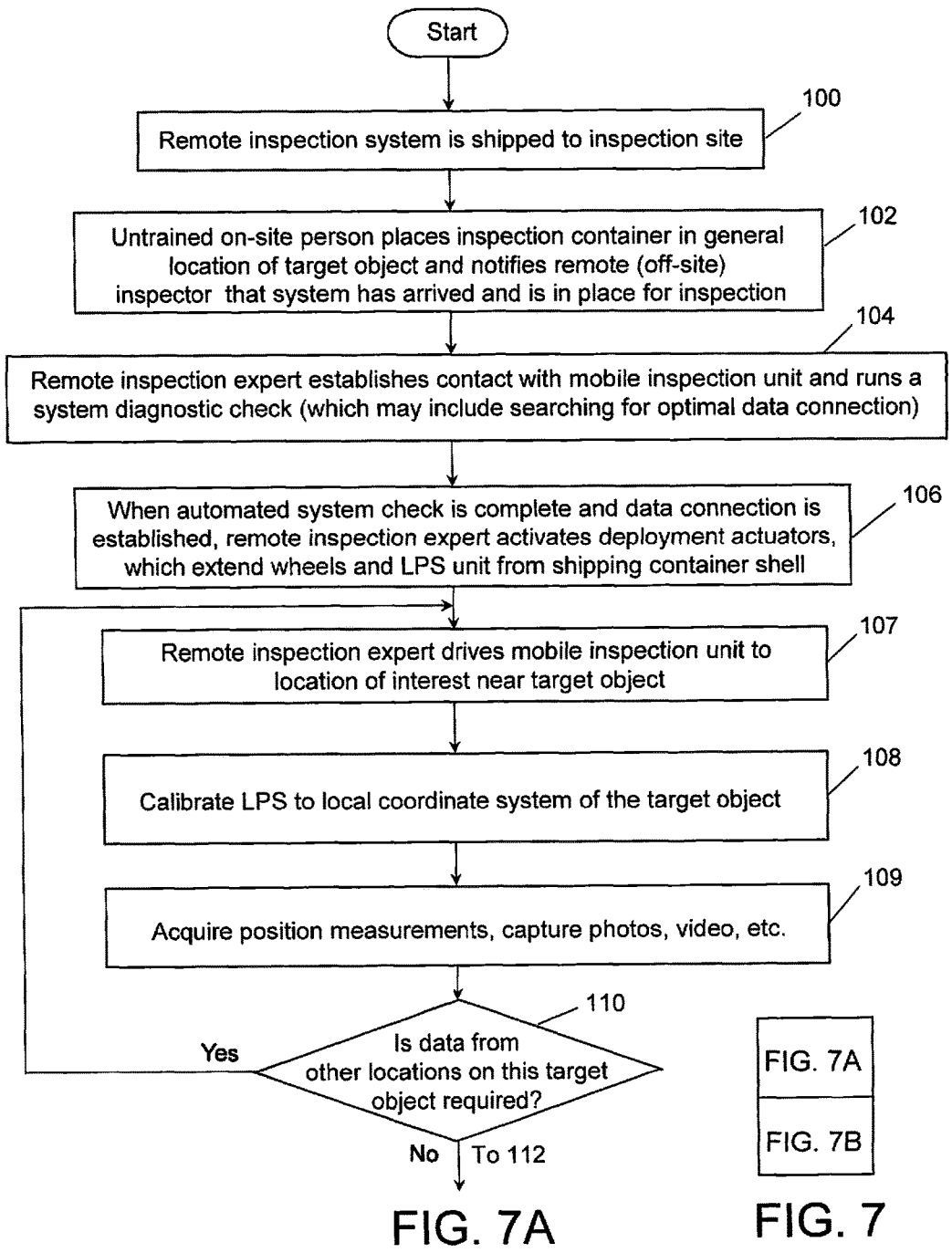

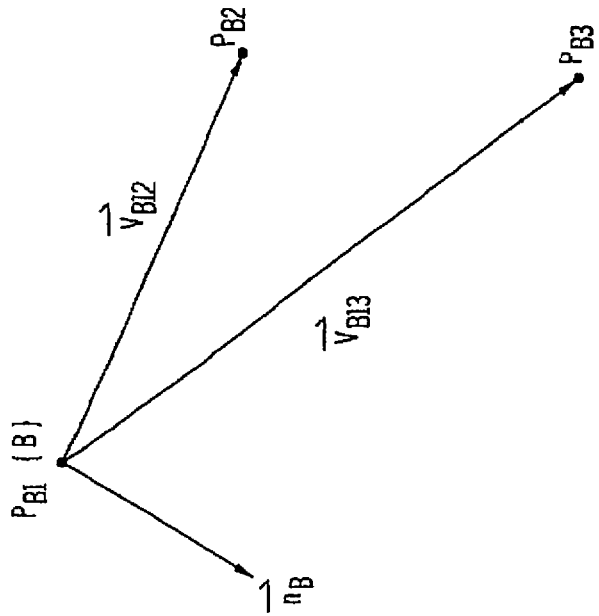
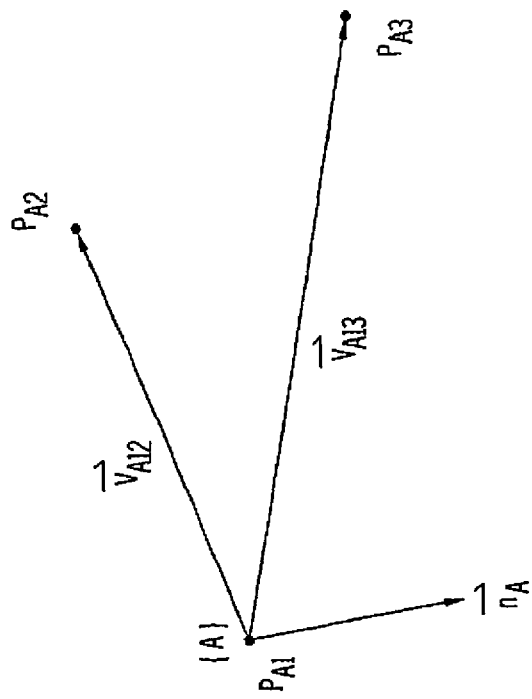
FIG. 9

REMOTELY OPERATED MOBILE STAND-OFF MEASUREMENT AND INSPECTION SYSTEM

RELATED PATENT APPLICATIONS

This application is a continuation-in-part of and claims priority from U.S. patent application Ser. No. 13/166,613 filed on Jun. 22, 2011, which issued on Nov. 10, 2015 as U.S. Pat. No. 9,182,487, and U.S. patent application Ser. No. 12/897,408 filed on Oct. 4, 2010, which issued on Jun. 3, 2014 as U.S. Pat. No. 8,744,133, the disclosures of which are incorporated by reference herein in their entirety.

The following additional patent applications are also incorporated by reference herein in their entirety: U.S. patent application Ser. No. 13/732,789 filed on Jan. 2, 2013; U.S. patent application Ser. No. 13/036,619 filed on Feb. 28, 2011; and U.S. patent application Ser. No. 12/235,161 filed on Sep. 22, 2008 (issued as U.S. Pat. No. 7,859,655 on Dec. 28, 2010).

BACKGROUND

The disclosure relates to position measurement for repair and maintenance management of vehicles such as aircraft. More particularly, the disclosure relates to a local positioning system and methods for non-destructive measurement and inspection of vehicles such as aircraft that do not require physical contact with the vehicle.

When repair work is required on vehicles, such as on the skin of an aircraft, it may be necessary to take into account the size, shape and location of previous damage and/or repairs for optimum repair of the vehicle. Photographs of the previous damage and/or repair may be made but may not be precisely located or sized on the vehicle or may not be useful for future repair planning. During the analysis of a damage/repair site (i.e., a location of interest), it may be desirable to obtain measurement information without contacting the target object. Due to accessibility and/or contact constraints, it may be difficult to reach the location of interest to obtain position measurements. Therefore it is advantageous for a local positioning system to be able to take measurements without contacting the target object and from moderate to large distances from the target object. Local positioning systems capable of stand-off measurement of a target object may utilize acoustic, laser-based, magnetic, RFID, GPS, and motion capture-based systems.

Finding and accurately measuring the locations of potential damage on a structure, such as a large commercial airplane, can be a laborious task. An efficient and automated process for addressing this problem would be valuable to many organizations involved in building and maintaining large vehicles and structures.

Prior inspection processes required inspection experts to be present with the measurement hardware at the site of the airplane (or other target object) being inspected. In accordance with that process, the inspection expert is required to travel to the inspection site, set up the equipment, and then perform the inspection. The end-to-end time requirement could be several days, depending on how far the expert had to travel.

Other semi-automated systems allowed remote operation of stationary measurement hardware, but still required an on-site assistant in order to set up and move the measurement instruments into position. One stand-off inspection system combines a local positioning system (LPS) with a nondestructive inspection (NDI) method to replace inspector's manual labor, increase the inspection rate, and find much smaller cracks than what can be seen visually, without physically touching the large target object. Another inspection system combines a stand-off local positioning system positioned adjacent to a large target object (i.e., at the inspection site) with an NDI scanner mounted to the target object. In accordance with the teachings of U.S. patent application Ser. No. 13/166,613 (from which this application claims priority), the system can be configured and programmed with remotely operated hardware and software components to enable data collection by an expert NDI analyst from an off-site operations center, with the only on-site assistance coming from non-expert support personnel to setup the local positioning system and NDI scanning hardware.

Furthermore, an NDI scanner mounted to a target object may perform less than ideally due to the contact between the sensor and the surface being inspected. For example, in-service NDI scans can be confusing because there any many structural elements (e.g., lightning protection, stiffeners, ramped back surfaces, etc.) that can add to the scan complexity. This can lead to extended inspection times, mistakes, or further inspections in order to increase the clarity of the results.

It would be advantageous if a remotely operable mobile system for NDI of a large target object, such as an airplane, could be set up at the inspection site with minimal on-site personnel assistance. In addition, it would be advantageous to employ a system for measurement and inspection which did not require contact with the target object. Accordingly, a mobile telepresence system capable of performing stand-off measurement and/or inspection of a large target object, such as an aircraft, would be advantageous.

SUMMARY

A self-contained, remotely operated, mobile measurement system for stand-off inspection of large target objects located at sites distant from an operations center of a distributed inspection system is disclosed herein. The system comprises a mobile platform with on-board instrumentation capable of making dimensional measurements in the local coordinate system of the target object. More specifically, the system comprises multiple hardware and software components networked to a control interface that enables the operator at the operations center to teleoperate the equipment, including driving the mobile platform to a region of interest, calibrating the on-board local positioning system, acquiring measurement and image data, and communicating with on-site personnel if needed. Additional types of remotely controlled sensors and actuators can also be added to the system.

The ability to operate all of the hardware and software components remotely enables data collection by an expert analyst from an off-site operations center, with minimal on-site assistance. A variation of the system is transformable from an integrated enclosure for shipping, to a mobile configuration for self-propelled movement to the inspection location, and then to a measurement acquisition configuration.

The ability of the inspection equipment to be self-contained and reconfigured remotely allows the remote operator of the system to be self-sufficient. It is not necessary to have a qualified person set up the measurement system at the inspection site. Additional system telepresence capabilities (such as two-way audio and video, plus the ability to point out locations) allow remote users of the system to interact with others at the inspection site if necessary.

One aspect of the subject matter disclosed in detail hereinafter is a mobile system comprising: a mobile platform; a drivetrain capable of moving the mobile platform; a local positioning system unit carried by the mobile platform, the local positioning system comprising: wave energy projecting means for projecting wave energy in a direction; directional control means for orienting the wave energy projecting means to project in a direction having a selected pan angle and a selected tilt angle; and means for detecting wave energy returned from the target object after each projection of wave energy; a wireless adapter capable of receiving commands from an in-range wireless network access point; first logic means for controlling the drivetrain to move the mobile platform relative to a target object in accordance with a platform location command received via the wireless adapter; and second logic means for controlling the local positioning system to project wave energy toward a plurality of points on the target object in response to calibration commands received via the wireless adapter.

The mobile system described in the preceding paragraph may further comprise third logic means for determining a position and an orientation of the wave energy projecting means relative to a coordinate system of the target object based on at least the following: (a) distances traveled by directionally projected wave energy detected by the wave energy detecting means after impingement on respective points on the target object; and (b) azimuth and elevation angles of the directional control means at times when wave energy was directionally projected.

Optionally, the mobile system may further comprise a shipping container, wherein the mobile system has first and second configurations, the local positioning system unit being disposed inside the shipping container when the mobile system is in the first configuration and outside the shipping container when the mobile system is in the second configuration. In that case the mobile system may further comprise means for reconfiguring the mobile platform and fourth logic means for activating the reconfiguring means to cause the mobile system to reconfigure from the first configuration to the second configuration in response to a deployment command received via the wireless adapter.

Another aspect of the subject matter disclosed herein is a mobile non-destructive inspection system comprising: a mobile platform; a drivetrain capable of moving the mobile platform; a pan-tilt mechanism carried by the mobile platform; an inspection unit capable of stand-off inspection of a surface area on a target object, the inspection unit being mounted to the pan-tilt mechanism; a directional projector of wave energy having a position and an orientation which are fixed relative to the position and orientation of the inspection unit and capable of distance measurement; a wave energy detector having a position and an orientation which are fixed relative to the position and orientation of the directional projector a wireless adapter capable of receiving commands from a wireless network access point when within range; a computer system programmed to execute the following operations: (a) control the drivetrain to move the mobile platform relative to a target object in accordance with a platform location command received via the wireless adapter; and (b) control the pan-tilt mechanism and the wave energy directional projector to project wave energy toward a plurality of points on the target object in response to a calibration command received via the wireless adapter. The computer system may be further programmed to determine a position and an orientation of the inspection unit relative to a coordinate system of the target object based on at least the following: (a) distances traveled by directionally projected wave energy detected by the wave energy detector after impingement on respective points on the target object; and (b) azimuth and elevation angles of the pan-tilt mechanism at times when wave energy was directionally projected.

A further aspect is a mobile system comprising: a mobile platform; a drivetrain capable of moving the mobile platform; a distance meter carried by the mobile platform and capable of stand-off measurement of a distance to a point measured along a direction vector; angle changing means for changing an azimuth angle and an elevation angle of the direction vector of the distance meter; a wireless adapter capable of receiving commands from an in-range wireless network access point; a computer system programmed to execute the following operations: control the drivetrain to move the mobile platform relative to a target object in accordance with a platform location command received via the wireless adapter, and control the angle changing means and the distance meter to measure respective distances and respective azimuth and elevation angles to a plurality of points on the target object in response to a calibration command received via the wireless adapter. Preferably the distance meter is a laser range meter.

Yet another aspect is a method for teleoperation of a self-powered mobile stand-off non-destructive inspection system from a command workstation, comprising: (a) establishing a communication channel between the self-powered mobile stand-off non-destructive inspection system and the command workstation via a wireless connection; (b) remotely controlling the stand-off non-destructive inspection system to move to a location near the target object; (c) remotely activating the stand-off non-destructive inspection system to calibrate its position and orientation relative to a coordinate system of a target object; and (d) remotely activating the stand-off non-destructive inspection system to acquire image data from a surface area of the target object without contacting that surface area. Optionally, the method may further comprise remotely activating the stand-off non-destructive inspection system to transform from a shipping configuration to a deployed configuration after step (a) and prior to step (b).

A further aspect of the disclosed subject matter is a method for determining a position and orientation of a video camera and measurement instruments of a mobile system relative to a coordinate system of a target object, comprising: establishing a communication channel between the mobile system and a command workstation at an operations command center via a wireless network access point; remotely controlling the mobile system to move to a location near the target object by transmitting a motion command from the command workstation; remotely activating the camera to transmit a video stream to the command workstation; while viewing the transmitted video stream at the command workstation, remotely controlling the orientation of the video camera until the video camera is oriented at azimuth and elevation angles whereat images of surface areas of the target object respectively include the respective calibration points; and remotely activating a distance meter of the mobile system by transmitting a calibration command from the command workstation, in response to which the distance meter will project wave energy in respective directions aimed at the respective calibration points, and then acquire distance data representing respective distances of the video camera from the respective calibration points.

Other aspects are disclosed in the detailed description that follows.

BRIEF DESCRIPTION OF THE DRAWINGS

FIGS. 9-11 are diagrams referred to in the Appendix, where an illustrative method for calculating a calibration matrix for coordinate system transformation is described.

Reference will hereinafter be made to the drawings in which similar elements in different drawings bear the same reference numerals.

DETAILED DESCRIPTION

Figure 1:
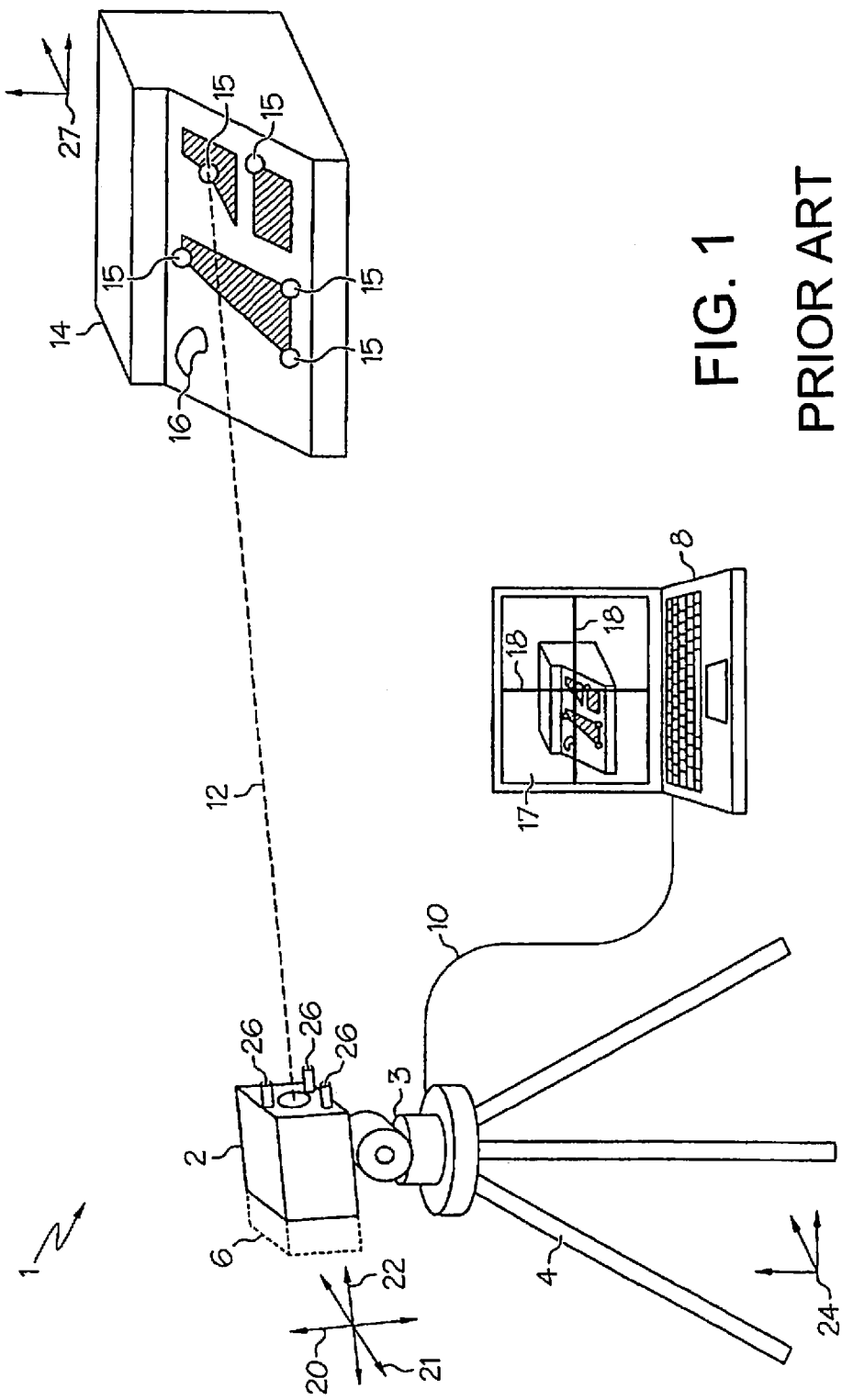
FIG. 1 is a diagram showing an isometric view of a known (not mobile) local positioning system.

The distributed system disclosed herein enables operation of one or more data collection devices from an off-site location without assistance from on-site personnel. The system comprises a self-contained, remotely operable, mobile system that can be utilized to acquire three-dimensional measurement and two-dimensional image data in accurately registered three-dimensional coordinates. This mobile stand-off measurement and inspection system can be operated by a remote expert at an operations center. The on-site system can be utilized to inspect an airplane (or other large target object) to determine precise locations in airplane coordinates, and then locate areas or parts of interest within the operating region. The system is equipped with a mobile platform that allows the off-site operator to drive the instrumentation to the inspection area without requiring any on-site setup. The communications between the system and the off-site operator can use a wired or wireless network connection. The system has on-board power; and when combined with wireless communications, the system can operate untethered.

For situations were the inspection equipment is shipped to a location and then returned, a variation in which the system is integrated into a shipping container can be used. When this system arrives at the inspection site it can connect to the wireless network, perform a systems check, and then when triggered by the off-site operator, re-configure into a state for mobile operation and stand-off inspection.

The distributed system with remotely operable stand-off inspection units disclosed herein leverages existing local coordinate measurement and remote operation techniques, specifically the capabilities of the local positioning systems described in the patent documents (identified above) which have been incorporated by reference herein. The non-mobile remote measurement and three-dimensional CAD integration aspects are disclosed in U.S. patent application Ser. No. 13/166,613 (now U.S. Pat. No. 9,182,487). The image data acquired by the video camera of the local positioning system may undergo image processing as disclosed in U.S. patent application Ser. No. 12/897,408 (now U.S. Pat. No. 8,744, 133). Alternatively, the remotely operable stand-off inspection units may be equipped with one or more stand-off NDI sensors of the types disclosed in U.S. patent application Ser. No. 13/732,789. The stand-off NDI technique employed can be selected from the following group: near-infrared spectroscopy, terahertz imaging, microwave imaging, x-ray backscatter imaging, stand-off infrared thermography, laser shearography, laser ultrasonic testing and laser vibrometry.

More specifically, U.S. patent application Ser. No. 12/897, 408 (now U.S. Pat. No. 8,744,133) discloses a method for detecting and determining a location of visible areas of change on a target object. The method comprises the steps of: determining a first position and orientation of a local positioning system with respect to the target object; determining an offset between the first position and orientation and a second position and orientation of a local positioning system previously utilized to collect a set of reference images of the target object, wherein determining the offset comprises computing an offset transformation matrix from the first position and orientation of the local positioning system to the second position and orientation of the local positioning system previously utilized to collect the set of reference images, the second position and orientation being in a coordinate system of the target object; repositioning, in position and orientation, the local positioning system with respect to the target object by the determined offset, wherein repositioning, in position and orientation, the local positioning system comprises utilizing the offset transformation matrix to reposition the local positioning system to substantially the second position and orientation of the local positioning system previously utilized to collect the set of reference images; utilizing the repositioned local positioning system to acquire a set of images of the target object from the second position and orientation; comparing the set of images to corresponding images within the set of reference images to detect a difference between the acquired set of images and the corresponding images within the set of reference images; and determining a location of the detected difference in the coordinate system of the target object. In accordance with one embodiment disclosed in U.S. patent application Ser. No. 12/897,408, the foregoing is accomplished by placing the local positioning system on a mobile platform. After the LPS unit is calibrated in its current position relative to the target object (which may be different from the initial reference position), the offset transformation matrix can be computed. The mobile platform then translates and rotates the LPS instrument by the same amounts to achieve realignment with the original position and orientation.

FIG. 1 depicts one embodiment of a local positioning system 1 suitable for providing position data on a target object defined in the local coordinate system of the target object. The local positioning system 1 may comprise a video camera 2 having automated (remotely controlled) zoom capabilities. The video camera 2 may additionally include an integral crosshair generator to facilitate precise locating of a point within an optical image field display 17 for displaying video camera output on a personal computer or other display device 8. In applications in which the crosshair generator is not an integral component of the video camera 2, a crosshair generator 6 (shown in phantom) may be connected to the video camera 2 as a separate element for this purpose or overlaid on the video stream on the personal computer or display device 8.

The video camera 2 shown in FIG. 1 (and also seen in FIG. 2, discussed later) is coupled to a motion-controlled pan-tilt mechanism 3 mounted on a stationary tripod support 4. The motion-controlled pan-tilt mechanism 3 may be capable of rotationally adjusting the video camera 2 to selected angles around the vertical, azimuth (pan) axis 20 and the horizontal, elevation (tilt) axis 21, as well as rotation of the video camera 2 to selected angles about a roll camera axis 22. For the implementation discussed here, measurement and control of the roll axis is not required.

Still referring to FIG. 1, a direction vector that describes the orientation of the camera relative to a fixed coordinate system 24 of the tripod 4 (or other platform on which the pan-tilt unit is attached) is determined from the azimuth and elevation angles, as well as the position of the center of crosshair marker in the optical field when the camera is aimed at a point of interest 16 on a target object 14. In FIG. 1, the direction vector is represented by line 12 which extends from the lens of camera 2 and intersects a location 15 on target object 14.

The specific implementation shown in FIG. 1 includes a plurality (e.g., three) of laser pointers 26 mounted on the camera 2 and aligned with the direction vector 12. Laser pointers 26 can be used to provide a visual indication on the target object 14 as to the aim or direction of the video camera 2. In an alternative embodiment (not shown in FIG. 1, but see FIG. 2), a laser range meter may be incorporated into the camera unit, which laser range meter can also perform the function of a laser pointer.

In the embodiment of a non-mobile local positioning system shown in FIG. 1, the video camera 2 and the pan-tilt mechanism 3 are operated by a personal or other computer 8. The computer 8 communicates with video camera 2 and pan-tilt mechanism 3 through a video/control cable 10. Control of the pan-tilt mechanism 3 and therefore, the orientation of the video camera 2 can be controlled using the keyboard of computer 8 or other input device. The optical image field 17, with crosshair overlay 18, as sighted by the video camera 2, can be displayed on the monitor of computer 8.

The local positioning system shown in FIG. 1 further comprises three-dimensional localization software which is loaded into computer 8. For example, the three-dimensional localization software may be of a type that uses multiple calibration points 15 on the target object 14 (such as a surface on an aircraft) to define the location (position and orientation) of video camera 2 relative to target object 14. The calibration points 15 may be visible features of known position (such as the corner of a window frame, a screw used to attach the pitot tube, etc.) in the local coordinate system 27 of the target object 14 as determined from a three-dimensional database of feature positions (e.g., a CAD model) or other measurement technique. During the LPS calibration process, X,Y,Z data for at least three non-collinear points are extracted from the CAD model. Typically calibration points are selected which correspond to features that can be easily located on the target object. The three-dimensional localization software utilizes the calibration points and the pan and tilt data from the pan-tilt mechanism 3 to define the relative position and orientation of the video camera 2 with respect to the local coordinate system 27 of the target object 14 (described in more detail below). The measured distances to the calibration points 15 may be used in coordination with the azimuth and elevation angles from the pan-tilt mechanism 3 to solve for the camera position and orientation relative to the target object 14.

Although the local positioning system shown in FIG. 1 is not mobile, the methodology for determining the position and orientation of a video camera (or other measurement instruments) mounted on a pan-tilt mechanism relative to the target object is equally applicable to a local positioning system incorporated in a mobile telepresence platform. Further details concerning this methodology, e.g., how to generate a camera pose transformation matrix reflecting the position and orientation of a video camera (and attached measurement instruments) relative to a coordinate system of the target object, are set forth in the Appendix.

Once the position and orientation of the video camera 2 with respect to the target object 14 have been determined, the computer 8 may be operated to rotate and zoom the optical image field of the video camera 2 to a desired location 16 of unknown position on the target object 14, which may be a damage/repair location on an aircraft, for example. At this position of the direction vector, the orientation of the video camera 2 (which may include the respective angles of the video camera 2 along the azimuth axis 20 and the elevation axis 21) may be recorded. By using the azimuth and elevation angles from the pan-tilt unit and the relative position and orientation of the camera determined in the calibration process, the location of the point of interest 16 can be determined relative to the coordinate system 27 of the target object 14. The damage/repair location 16 on the target object 14 may be sized by aligning the crosshairs 18 in the optical image field of the video camera 2 along the boundary of the damage/repair location. In the case of a crack, the length of the crack may be measured by moving the crosshairs from one tip of the crack to the other tip of the crack, traveling along the crack path.

The reverse process, in which the position of a point of interest 16 may be known in the target objects coordinate system (from a previous data acquisition session, a CAD model, or other measurement), can also be performed. In this situation, the camera may be placed in any location on the work area where calibration points are visible (which may be in a different location than the location where the original data was recorded) and the instrument-to-target calibration step may be performed. This calibration is sometimes referred to as the camera pose, and will be referred to that here as well, but it is associated with more than just the camera; for example, it may also include instrumentation for measuring distance (such as a laser range meter). The direction vector 12 from the point of interest to the camera 2 may be calculated in the target objects coordinate system 27. The inverse of the camera pose transformation matrix may be used to convert the direction vector into the coordinate system of the camera. The azimuth and elevation angles may then be calculated and used by the pan-tilt unit to aim the camera 2 at the point of interest on the target object 14.

In a typical implementation, the LPS instrument may be set up within about 10-50 feet of the target object 14. The target object 14 may, for example, be a surface of an aircraft that is equipped with an array of dielectric tops. The calibration points 15 on the target object 14 may be selected and used by the three-dimensional localization software (loaded in computer 8) in conjunction with the pan and tilt data (i.e., azimuth and elevation angles) from the pan-tilt mechanism 3 to determine the position and orientation of the video camera 2 with respect to target object 14. The calibration points 15 may be feature points of known position in the local coordinate system 27 of the target object 14 as determined from a three-dimensional CAD model or other measurement technique. In some implementations, the pan-tilt unit 3 may be attached to a portable support such as a tripod 4. In other implementations, the pan-tilt unit could be attached to a stationary support, such as the walls of an airplane hangar.

The three-dimensional localization software loaded onto the computer 8 can be utilized to determine the position and orientation of the video camera 2 with respect to the target object 14 and generate a camera pose transformation matrix using one of three known methods: (1) a vector-based approach; (2) position and orientation based on 5- or 7-point technique; and (3) a laser range-based system. The vector-based approach may utilize three calibration points 15 on the target object 14 and solve simultaneous equations to determine the position of the video camera 2 with respect to the target object 14. This assumes the relative orientation of the camera is known. The position and orientation calibration based on 5- or 7-point techniques may determine both the position (X,Y,Z) and the orientation (roll, pitch, yaw) of the video camera 2 relative to the target object 14. The 5-point method may utilize five known calibration points 15 that all lie on the same planar surface of the target object 14. The 7-point method may utilize seven known calibration points 15 that are not all on the same planar surface of the target object 14.

Optionally, an off-the-shelf laser-based distance measurement device, such as a laser range meter (also called "a laser distance meter") may be integrated into the video camera to create a laser hybrid system. (The laser range meter is not visible in FIG. 1 because it is inside the camera housing.) This laser range meter/video camera hybrid system may be incorporated onto the pan-tilt mechanism. Measurement data from the laser range meter can be used to obtain estimates of the respective distances from the laser range meter (i.e., from the video camera) to calibration points on a target object. A typical laser range meter comprises a laser diode which transmits a bundled, usually visible, laser beam toward a surface of a target object. The light which is backscattered and/or reflected by the target object is imaged on the active surface of a photoreceiver by receiving optics. The laser diode has a position and an orientation which are fixed relative to the position and orientation of the video camera; the photoreceiver has a position and an orientation which are fixed relative to the position and orientation of the laser diode. The time of flight between transmission and reception of the light can be used to calculate the distance between the laser range meter and the portion of the target object surface on which the transmitted beam impinged. The laser range meter also functions as a laser pointer. Alternatively, a distance meter which directionally projects wave energy other than a laser beam could be utilized.

Figure 2:
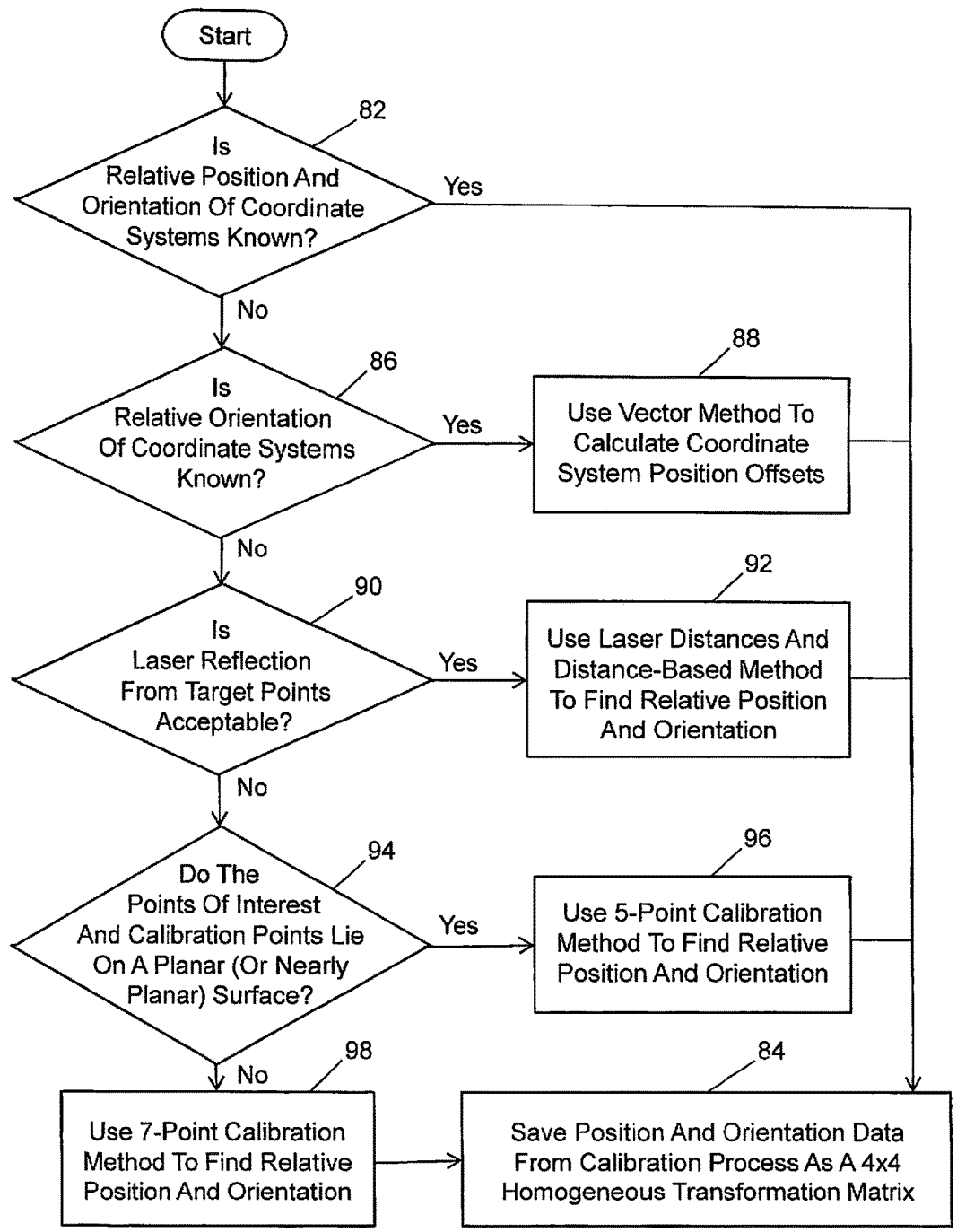
FIG. 2 is a flowchart showing steps of a method for generating an instrument to target calibration transformation matrix (sometimes referred to as the camera pose) in accordance with one embodiment, which method can be utilized by both mobile and non-mobile local positioning systems.

FIG. 2 is a flowchart showing steps of a method for generating a camera pose transformation matrix in accordance with one embodiment, which method can be utilized by both mobile and non-mobile local positioning systems. In step 82, a determination is made whether the relative position and orientation of the coordinate systems of the video camera and the target object are known or not. If the decision made in step 82 is affirmative, then the position and orientation data from the calibration process is saved as a 4×4 homogeneous transformation matrix in step 84.

If the decision made in step 82 is negative (i.e., at least one of the relative position and relative orientation of the coordinate systems is unknown), then a determination is made in step 82 whether the relative orientation of the coordinate systems is known or not if the decision made in step 86 is affirmative (i.e., the relative orientation of the coordinate systems is known), then a vector method (step 88) may be used to calculate coordinate system position offsets. The position and orientation data derived from the calibration process in step 88 are then saved as a 4×4 homogeneous transformation matrix (step 84).

If the decision made in step 86 is negative (i.e., the relative orientation of the coordinate systems is not known), then a determination is made in step 90 whether laser reflections from the calibration points on the target object are acceptable or not. If the decision made in step 90 is affirmative (i.e., the laser reflections from the calibration points on the target object are acceptable), then the laser distances and a distance-based method may be used (step 92) to calculate the position and orientation of the camera relative to the target object (i.e., calculate the position and orientation of the coordinate system of the camera relative to the coordinate system of the target object. The position and orientation data derived from the calibration process in step 92 are then saved as a 4×4 homogeneous transformation matrix (step 84).

If the decision made in step 90 is negative (i.e., the laser reflections from the calibration points on the target object are not acceptable), then a determination is made in step 94 whether the calibration points and the points of interest lie on a planar or nearly planar surface or not if the decision made in step 94 is affirmative (i.e., the calibration points and the points of interest lie on a planar or nearly planar surface), then a 5-point calibration method (step 96) is used to calculate the position and orientation of the camera relative to the target object. The position and orientation data derived from the calibration process in step 96 are then saved as a 4×4 homogeneous transformation matrix (step 84).

If the decision made in step 94 is negative (i.e., the calibration points and the points of interest do not lie on a planar or nearly planar surface), then a 7-point calibration method (step 98) is used to calculate the position and orientation of the camera relative to the target object. The position and orientation data derived from the calibration process in step 98 are then saved as a 4×4 homogeneous transformation matrix (step 84).

Returning to FIG. 1, once the position and orientation of the video camera 2 with respect to the target object 14 have been determined and the camera pose transformation matrix has been generated, camera pan data (angle of rotation of video camera 2 about the azimuth axis 20) and tilt data (angle of rotation of video camera 2 with respect to the elevation axis 21) may be used in conjunction with the calculated position and orientation of video camera 2 to determine the (X,Y,Z) position of any point of interest (such as the damage/repair location on the skin of the aircraft) in the coordinate system of the target object 14. The video camera 2 may then be aimed at the damage/repair location on the target object 14, with the center and/or outline of the damage/repair location defined.

Because the position of the damage/repair location on the target object 14 may not initially be known, the pan and tilt angles of the pan-tilt mechanism 3 may be used to determine the direction vector 12 in the local camera coordinate system 24 of the video camera 2. Determination of the surface position of the damage/repair location may be made by any one of the following methods: (1) an approximation using the ray intersection from a polygonal surface formed from the calibration points, or other user-selected features of known position on the target object; (2) three-dimensional data from a CAD model, for example; or (3) the distance from the optional laser-based measurement device. At this stage, the camera pose transformation matrix may be used to transform or convert the damage/repair location, which is initially defined in the local coordinate system of video camera 2, into the local coordinate system of target object 14.

A three-dimensional model coordinate system and maintenance database of the target object 14 may then be accessed by computer 8 to locate previous locations of damage, repairs and/or other issues on the target object 14. Present repair of the damage/repair location on the target object 14 may then be planned and completed based on the positional and geometric relationships of the previous damage, repairs and/or issues with the damage/repair location. The positional and geometric information of the video camera 2 when its optical image field is aimed at the damage/repair location may be saved and superimposed on the three-dimensional model, which may be maintained in a database. Digital photographs of the damage/repair location may additionally be taken using the video camera 2 or other camera and saved in the database. Accordingly, the updated database is available in the event that a subsequent repair of the target object 14 is called for.

Figure 3:
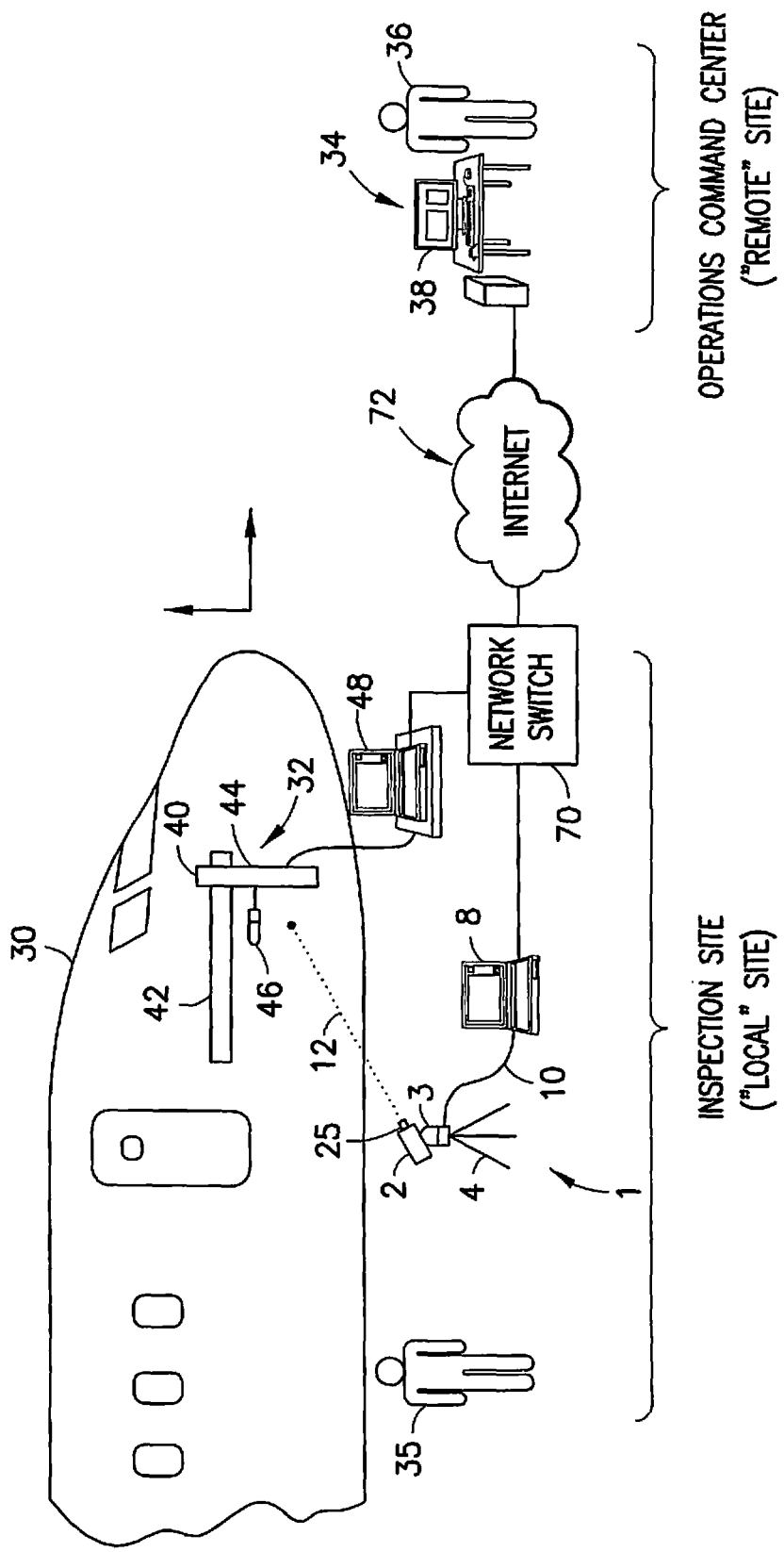
FIG. 3 is a diagram showing components of a distributed system for measuring and inspecting an aircraft at a local site, as disclosed in U.S. patent application Ser. No. 13/166, 613. The inspection system combines a stand-off local positioning system positioned adjacent to an aircraft at the inspection site with an NDI scanner mounted to the target object, which systems are set up with the assistance of on-site personnel.

FIG. 3 shows an acquisition and analysis system for non-destructive inspection employing multiple hardware and software components (including a local positioning system) networked through a central analysis interface. (The local positioning system shown in FIG. 3 may be of the type described with reference to FIGS. 1 and 2.) The integration of these components enables a remote operator to acquire and analyze NDI data using automated scanning equipment and a local positioning system, and then visualize and interact with the data in two- and three-dimensional analysis software. Alignment points measured by the local positioning system in the scanning area are used to create a positional correspondence for setup of the scanning equipment and registering the resulting two-dimensional scan data in the coordinate system of a three-dimensional CAD model visualization environment. The ability to operate all of the hardware and software components remotely enables data collection by an expert NDI analyst located at an off-site operations center, with the only on-site assistance coming from non-expert support personnel to setup the LPS and NDI scanning hardware.

The primary on-site and off-site hardware components of the system shown in FIG. 3 will now be described. A local positioning system 1 for determining local three-dimensional coordinates of an aircraft 30 and an NDI scanner 32 are located at the inspection site (referred to herein as the "local site"). A command workstation 34 (to be operated by an NDI expert 36) is located at an operations command center (referred to herein as the "remote site") with a master display 38. The NDI scanner 32 comprises a scanning unit 40 having a support rail 42 mounted on the aircraft and a translation rail 44 supporting an ultrasonic head 46. The translation rail 44 moves along the support rail 42 for a first scan axis and the head 46 moves along the translation rail 44 for a second scan axis, which can be perpendicular to the first scan axis. The NDI scanning unit is controlled by a second control PC 48.

For conducting remote NDI operations, tasks performed by a support technician 35 at the inspection site include: removing the local positioning system 1 and NDI scanner 32 from shipping/storage containers; setting up the local positioning system 1; attaching the NDI scanner 32 to the aircraft 30; and connecting the control PCs 8, 48 to the Internet 72 by way of a network switch 70. The Internet connection of the control PCs may be wired or wireless. After setup, the local positioning system 1 allows an NDI expert 36 at the remote site to help guide the rest of the process, as will be described in greater detail hereinafter. Once the control PC 8 is started, an automated process will send the on-site network domain information back to the operations center via network switch 70 and the Internet 72.

The NDI scanning aspects of the system shown in FIG. 3 are not germane to the mobile stand-off inspection system that will be disclosed in detail later with reference to FIGS. 4 through 7, but the local positioning aspects of the system shown in FIG. 3 are germane and will be described in further detail here.

Still referring to FIG. 3, when the on-site setup of the local positioning system 1 has been completed by the on-site support technician 35, the NDI expert 36 at the operations center connects to the LPS control PC 8 through a network socket connection (not shown) in the remote workstation 34 to operate a LPS pan-tilt unit 3, a video camera 2, and a laser range meter 25 (which also functions as a laser pointer) using an LPS graphical user interface (GUI) (not shown) and a manual controller (not shown). A video connection is also established through an LPS video server (not shown). The visual display of the LPS GUI and associated video from the local positioning system 1 are displayed on the master display 38. The LPS GUI allows communication of position data as well as camera/video data from the local positioning system 1 to the command workstation 34, and control of the local positioning system for positioning, orientation and operation of the camera 2 and laser range meter 26 from the command workstation.

The measurement and inspection system shown in FIG. 3 can be improved by employing a stand-off (i.e., non-contact) NDI system instead of a contact-type NDI system and by substituting a mobile local positioning system for a stationary system, as described in more detail below.

Figure 4:
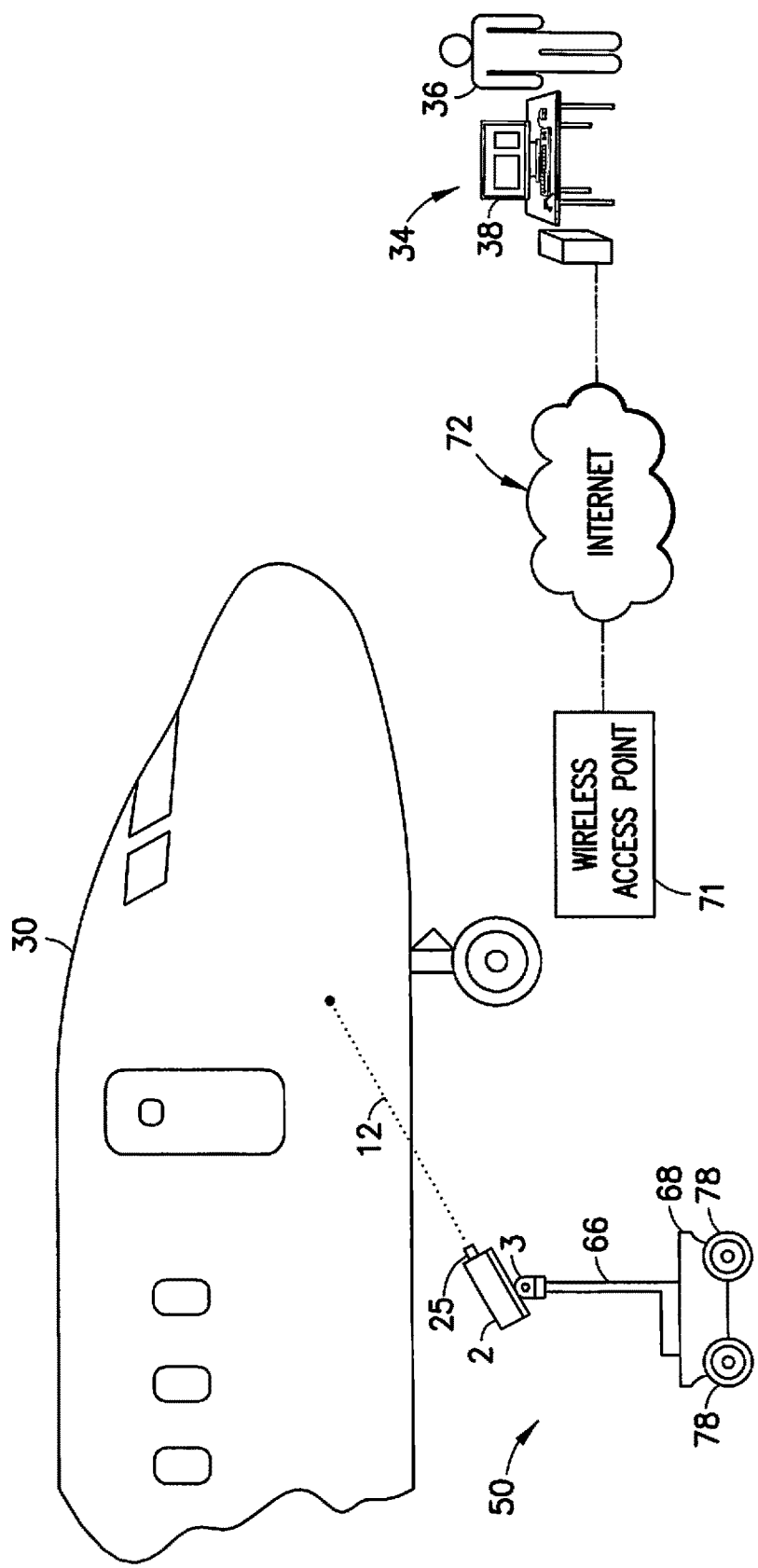
FIG. 4 is a diagram showing components of a distributed system for stand-off measurement and inspection of an aircraft at a site distant from an operations center of a distributed inspection system with minimal on-site personnel assistance.

FIG. 4 shows components of a distributed system for stand-off measurement and inspection of an aircraft 30 at a site distant from an operations command center with minimal on-site personnel assistance. This expanded implementation of the distributed system comprises a battery-powered mobile measurement system 50 situated on the ground at the inspection site. In accordance with the embodiment depicted in FIG. 4, system 50 combines a mobile platform 68 having four wheels 78 (only two of which are visible) with an LPS unit mounted to a vertical pole 66. The LPS unit comprises a video camera 2, a pan-tilt mechanism 3 and a laser range meter 25 of the types previously described. The mobile measurement system 50 further comprises means (not shown in FIG. 4) for communicating with a wireless network access point 71, which in turn enables communication with a command workstation 34 at an operations command center via the Internet 72. Movement of the platform 68 and operation of the LPS unit can be controlled remotely by an NDI expert 36 situated at the operations command center. The components can be controlled by a wireless connection, or by tethered connection if necessary. Optionally, the mobile measurement system may be collapsible for shipping purposes, in which case the system may be provided with one or more deployment actuators that can be operated under the control of the NDI expert at the operations command center. The system components may be ruggedized to withstand the rigors of shipping.

Because the mobile measurement system 50 shown in FIG. 4 can be operated remotely, it can be controlled by an off-site NDI expert 36 with minimal on-site support. The tasks performed at the inspection site include receiving the mobile measurement system 50 from a shipping company, moving the mobile measurement system to or closer to the inspection site, and making sure that there is a relatively clear path for the mobile system to access the airplane. The ability to set up the system by commands sent via wireless communication allows an off-site NDI expert 36 to perform inspection and measurement of the aircraft 30 without requiring on-site personnel to setup the inspection equipment. The off-site NDI expert 36 can also provide guidance to an on-site repair team using the laser range meter 25 as a laser pointer, as well as using integrated audio and display capabilities on the mobile platform.

The ability to communicate with and control the operation of the mobile measurement system provides a telepresence platform that allows the off-site NDI expert 36 to explore the inspection environment and use the on-board LPS capabilities to acquire position measurements in either a point-to-point form or in Cartesian coordinates of the local coordinate system of the target object (in this case, an aircraft 30). Additional two-way audio and display components may be added to the mobile measurement system to extend the functionality to that of a full telepresence platform capable of performing measurements.

The mobile measurement system 50 can be used to determine the exact position of an in-service NDI scan in airplane coordinates and then the NDI expert 36 can use that information to retrieve the exact CAD data that matches the stand-off NDI scan, and then provide an overlay of the underlying airplane structure on top of the NDI image using the airplane CAD data.

The mobility of the platform enables the acquisition of measurements defined in terms of the local coordinate system of the target object with the freedom to move the measurement system around at the inspection site. The ability to acquire measurements from a mobile platform is an important capability for off-site inspectors and maintenance personnel, and also as a tool for designers and managers for initial manufacturing.

The mobile platform 68 may be a holonomic motion vehicle. The vehicle may also have an on-board position and orientation tracking system that may comprise a set of omni wheels arranged in a four-omni wheel, perpendicular, double-differential odometry configuration of the type disclosed in U.S. patent application Ser. No. 13/796,584. Adding a real-time tracking system, such as multi-axis odometry, to the mobile platform allows the system to be controlled at a higher level, such as by instructing it to move to specific coordinates instead of requiring the remote operator to drive the platform directly. This also enables the mobile platform to be programmed to automatically follow a specified path plan, which may include returning to a specific location where prior LPS measurements or images were recorded. Even if the tracking system could only produce a rough estimate, measurements made by the mobile local positioning system could be used to determine a more accurate location of the platform relative to the target object.

As with other mobile telepresence systems, a mobile platform, camera, microphone, and speaker can part of the full system. On-board lighting and environmental sensors, such as weather station sensors (temperature, humidity, wind speed) or proximity sensors (for collision avoidance), may also be included on the mobile platform. Additional inspection sensors, such as the stand-off NDI sensors disclosed in U.S. patent application Ser. No. 13/732,789, may also be part of a mobile measurement and inspection system. In these cases, NDI, measurement, telepresence and guidance capabilities enables the entire inspection to be accomplished remotely.

Figure 5:
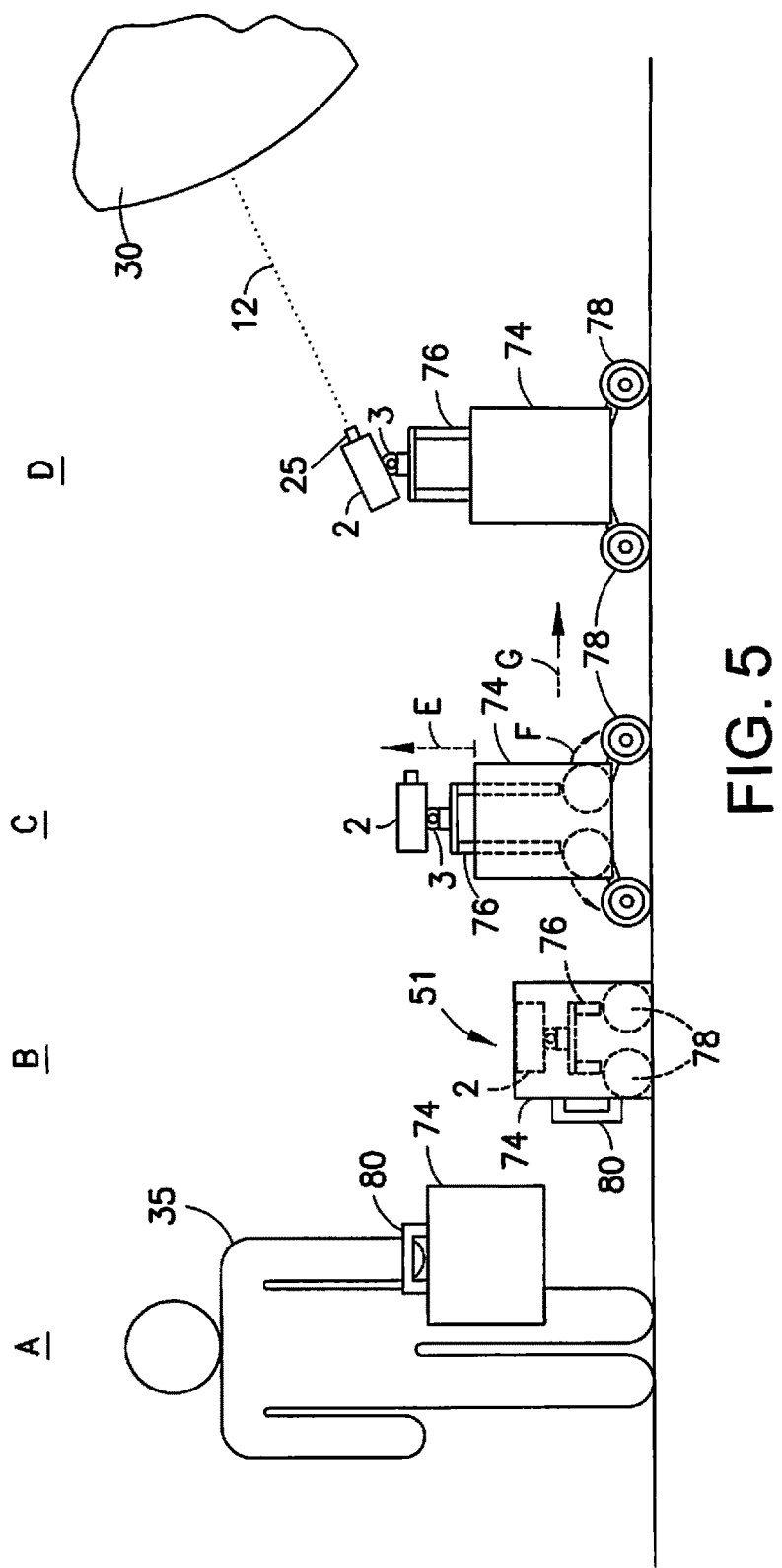
FIG. 5 is a diagram showing three configurations of a self-contained, remotely operable, mobile measurement system for stand-off inspection of large target objects in accordance with one on-site usage scenario.

In some situations where the mobile measurement system is shipped to the inspection site, it can be useful to package all of the on-site inspection components into a single, reusable shipping container. Such a self-contained measurement system is shown in FIG. 5. Having the inspection system integrated with the shipping container 74 has the advantage that the on-site technician 35 need not unpack components from the container or re-pack them when the inspection is complete. The shipping container 74 serves as a protective shell during shipment for the systems components, including deployable components intended to contact or interact with the environment at the inspection site. The shipping container may comprise motorized doors which open to allow extension of the deployable components and reclose after retraction of those same components. Additional display elements may be integrated into the exterior of the container, such as an integrated electronic label (i.e., an externally visible display that uses electronic ink) that can be used to show shipping information on the exterior of the container. This can be changed remotely to provide the destination information for return shipment.

The self-contained, remotely operable, mobile measurement system 51 shown in FIG. 5 comprises a shipping container 74 and various deployable subassemblies which fit inside the container when retracted and protrude outside the container when extended. These subassemblies can be deployed in response to commands received, from an NDI expert 36 at the operations command center.

FIG. 5 shows three configurations of the mobile measurement system 51 for stand-off inspection of large target objects in accordance with one on-site usage scenario. For this example, the video camera 2 will perform the stand-off inspection function (such as the functionality disclosed in U.S. patent application Ser. No. 12/897,408). The configurations shown in FIG. 5 would also be applicable to mobile inspection systems that used other types of stand-off NDI sensor units.

FIG. 5 depicts four stages A through D which occur successively over time at the inspection site. Part A of FIG. 5 shows a support technician 35 carrying a self-contained mobile measurement system 51 to or toward the inspection site. In the implementation shown, system 51 comprises a container 74 with a handle 80.

Figure 6:
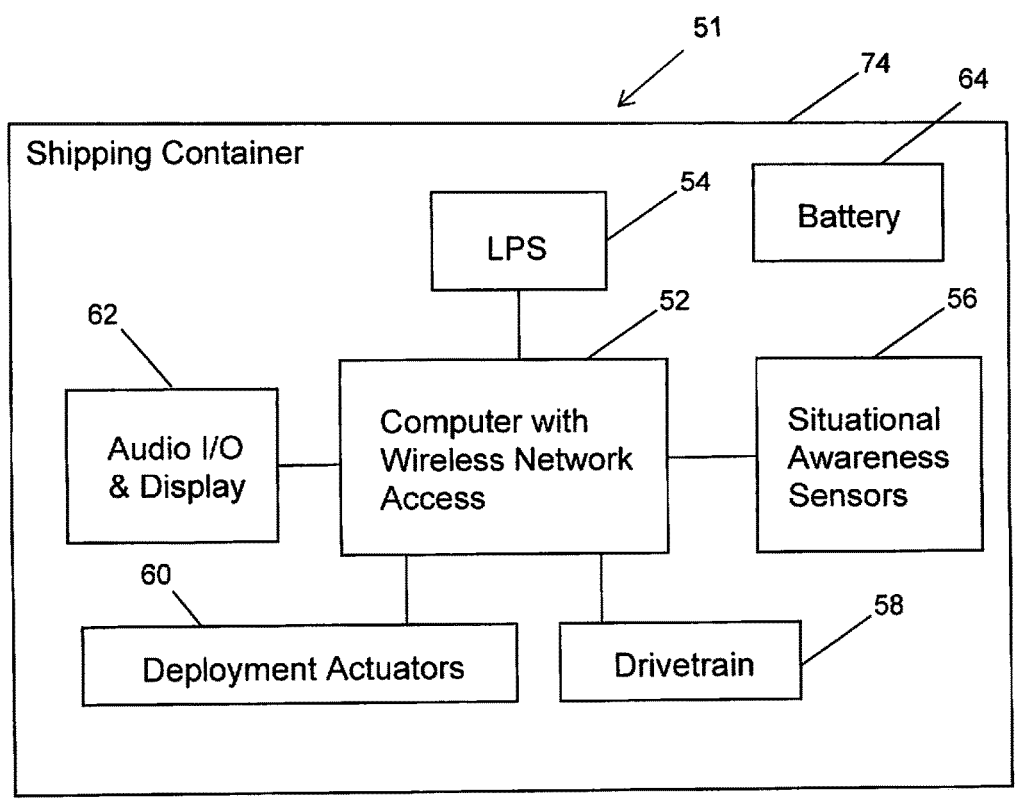
FIG. 6 is a diagram showing hardware and software components of a self-contained, remotely operable, mobile measurement system for stand-off inspection of target objects in accordance with one embodiment.

Other system components are disposed inside the container 74 when the system is in its shipping configuration. FIG. 6 shows the following internal components: a computer 52 with wireless network access (e.g., via an internal or external wireless adapter); an LPS unit 54 that communicates with computer 52; situational awareness sensors 56 which communicate with computer 52; a drivetrain 58 comprising at least one actuator (such as an electric motor) which communicates with computer 52; deployment subsystem 60 comprising at least one actuator which communicates with computer 52; and audio input/output and display units which communicate with computer 52. All electrical devices are powered by an electrical power source, such as a battery 64.

Returning to FIG. 5, Part B shows the measurement system 51 (partly depicted in FIG. 6) in its retracted configuration after the technician 35 has placed the system on the ground. The container 74 may be provided with marking to indicate which face should be placed in contact with the ground for proper pre-deployment placement. For proper deployment, the system 50 must be placed upright with wheels 78 under the LPS unit (see item 54 in FIG. 6). After the technician has placed the self-contained system at a desired location, the technician has no further role to play until the automated inspection has been completed and the system is destined to be shipped back to the operations command center (or other warehousing location).

The NDI expert at the operations command center has the ability to send commands to the on-board computer of the mobile measurement system. To activate deployment, the NDI expert sends a command which causes the on-board computer to activate the one or more deployment actuators to cause extension (by translation and/or rotation) of the deployable components. As a result of these motions, the system adopts a measurement configuration in which the deployable components (e.g., video camera, laser range meter, and wheels) extend out of the shipping container 74. Part C of FIG. 5 shows the system 51 during extension of the deployable components. The vertical dashed arrow E indicates that LPS unit is being extended upward; the curved dashed arrows F indicate that wheels 78 are being pivoted outward in opposite directions along respective arcs.

As best seen in Part C of FIG. 5, one deployable subassembly of the mobile measurement system comprises the LPS unit (including video camera 2 mounted to pan-tilt mechanism 3) and an extendible/retractable support frame 76 (shown in an extended state in FIG. 5) to which the pan-tilt mechanism 3 is attached. When support frame 76 is retracted, the video camera 2 and pan-tilt mechanism 3 will be housed inside the container 74. The support frame 76 may comprise a pair of telescoping arms. Alternatively, the extendible/retractable support frame 76 can be slidably coupled to a container frame (a rigid internal part of the shipping container 74) in a well-known manner (e.g., by means of linear guide halves respectively mounted to the support frame 76 and the container frame). In one implementation, a linear deployment actuator (not shown in FIG. 5) is installed inside the container 74. For example, the linear actuator may comprise a lead screw (not shown) threadably coupled to a lead screw nut (not shown) that is attached to the support frame 76, so that the latter extends or retracts depending on the direction in which the lead screw is rotated. The lead screw can be coupled to the output shaft of an electric motor (not shown), also housed inside the container 74. Other types of electromechanical linear actuators, capable of being powered by a battery, can be used.

Another deployable subassembly, which fits inside the container 74 when retracted and protrudes outside the container 74 when extended, comprises four wheels 78 (only two of which are visible in FIG. 5) and associated mechanisms (e.g., wheel axles, rotary encoders, etc.). At least one of the wheels 78 is a drive wheel that receives torque from the drivetrain and provides the final driving force for the mobile measurement system. Each wheel 78 may be mounted to a respective axle which is pivotably mounted at a distal end of a respective deployable arm (not shown). In accordance with one implementation, four deployable arms may be coupled together so that they al rotate in unison in response to activation of an actuator. In one implementation, a rotary deployment actuator (not shown in FIG. 5) is installed inside the container 74. For example, the rotary actuator may comprise a set of gears (not shown), including respective gears mounted to each axle, one gear mounted to the output shaft of an electric motor (not shown), and other intervening gears which couple the axle-mounted gears to the shaft-mounted gear. Other types of electromechanical rotary actuators, capable of being powered by a battery, can be used. In some embodiments (not shown in FIG. 5), a single actuator may be used to deploy both the LPS unit and the wheels using a mechanical linkage connecting both subsystems to the same actuator.

After the deployable components have been deployed (at which time the mobile measurement system 51 will be in its measurement configuration), the NDI expert sends a command which causes the on-board computer to activate the drivetrain to move the mobile measurement system 51 to a desired location. This movement is indicated by arrow G in FIG. 5. After the system has been positioned at the commanded location, the NDI expert can send commands to the on-board computer instructing the LPS unit to begin the calibration.

The mobile measurement system comprises on-board instrumentation capable of making dimensional measurements in the local coordinate system of the target object. More specifically, the on-board computer (item 52 in FIG. 6) can be loaded with three-dimensional localization software of a type that uses multiple calibration points on the aircraft (item 30 in FIG. 5) to define the location (position and orientation) of video camera 2 relative to aircraft. The calibration points may be visible features of known position (such as the corner of a window frame, a screw used to attach the pitot tube, etc.) in the local coordinate system of the aircraft as determined from a three-dimensional database of feature positions (e.g., a CAD model) or other measurement technique.

Part D of FIG. 5 shows the mobile measurement system in its measurement configuration as the LPS unit directs a laser beam at a calibration point on the aircraft 30. The three-dimensional localization software utilizes the calibration points (i.e., light reflected from the calibration points in response to impinging laser beams transmitted by the laser range meter of the LPS unit) and the pan and tilt data from the pan-tilt mechanism 3 to define the relative position and orientation of the video camera 2 with respect to the local coordinate system of the aircraft 30. The measured distances to the calibration points may be used in coordination with the azimuth and elevation angles from the pan-tilt mechanism 3 to solve for the camera position and orientation relative to the aircraft. The on-board computer may be further programmed to generate a camera pose transformation matrix reflecting the position and orientation of the video camera relative to the coordinate system of the aircraft.

In accordance with alternative embodiments, the three-dimensional localization software can be hosted on a computer at the operations command center, which computer receives distance and pan-tilt angle information from the mobile local positioning system for use in calculating a camera pose coordinate transformation matrix.

More specifically, there are two ways that the point measurement data for calibration can be acquired: (1)

manual acquisition (teleoperation) and (2) automated acquisition (in which the LPS unit and processing software finds the calibration points itself).

(1) In the manual process, three non-colinear points are required for which the X,Y,Z positions are known and defined in the aircraft coordinate system. These points can come from any trusted source, for example: CAD data or prior measurement with another system. When CAD data is used, the NDI expert at the operations command center visually finds the points by selecting them in a CAD model visualization environment (or equivalently from data stored from a prior session), and saves the X,Y,Z data for each point (to a file or memory). With the LPS unit active and connected to the network, the images acquired by the video camera of the mobile local positioning system are sent back to the operations command center for viewing on the display screen of the command workstation. Then the NDI expert visually finds the same points on the aircraft by remotely controlling the direction in which the video camera of the mobile local positioning system is aimed and saves the pan, tilt, and distance measurements for each calibration point. Using the known and measured data, the calibration process (set forth in more detail in the Appendix) computes the 4×4 homogeneous transformation matrix that defines the position and orientation of the camera relative to the aircraft (sometimes called the "camera pose").

(2) For the automated process, the mobile local positioning system can use its on-board camera and image processing software in some conditions to find features on the aircraft and associate those features with their known three-dimensional data points. Automated feature tracking is possible using two-dimensional image processing software, in situations where the same high-contrast calibration points that were initially selected by the NDI expert are continuously visible during movement of the local positioning system to a new location, then those two-dimensional image features can be used to direct the local positioning system to acquire new three-dimensional points using those two-dimensional locations (which are converted into pan and tilt angles for local positioning system aiming, and then laser distance acquisition). The on-board computer of the mobile local positioning system can then use the acquired data to compute a new camera pose transformation matrix. If the motion of the mobile local positioning system is too large for the same calibration features to remain visible throughout the motion path to the new location, the system can signal the NDI expert at the operations command center that manual recalibration is required. To minimize the distance that the mobile local positioning system will travel during the automated calibration process, preferably before the latter process is started, the NDI expert will drive the mobile local positioning system to a location near to location whereat the inspection will be performed. In order for the automated process to work, the local positioning system should be manually calibrated once at the start (i.e., an initial calibration). Thereafter computer on board the mobile local positioning system can recalibrate after each movement. After the system has been calibrated, the inspection process can begin.

Figure 7B:
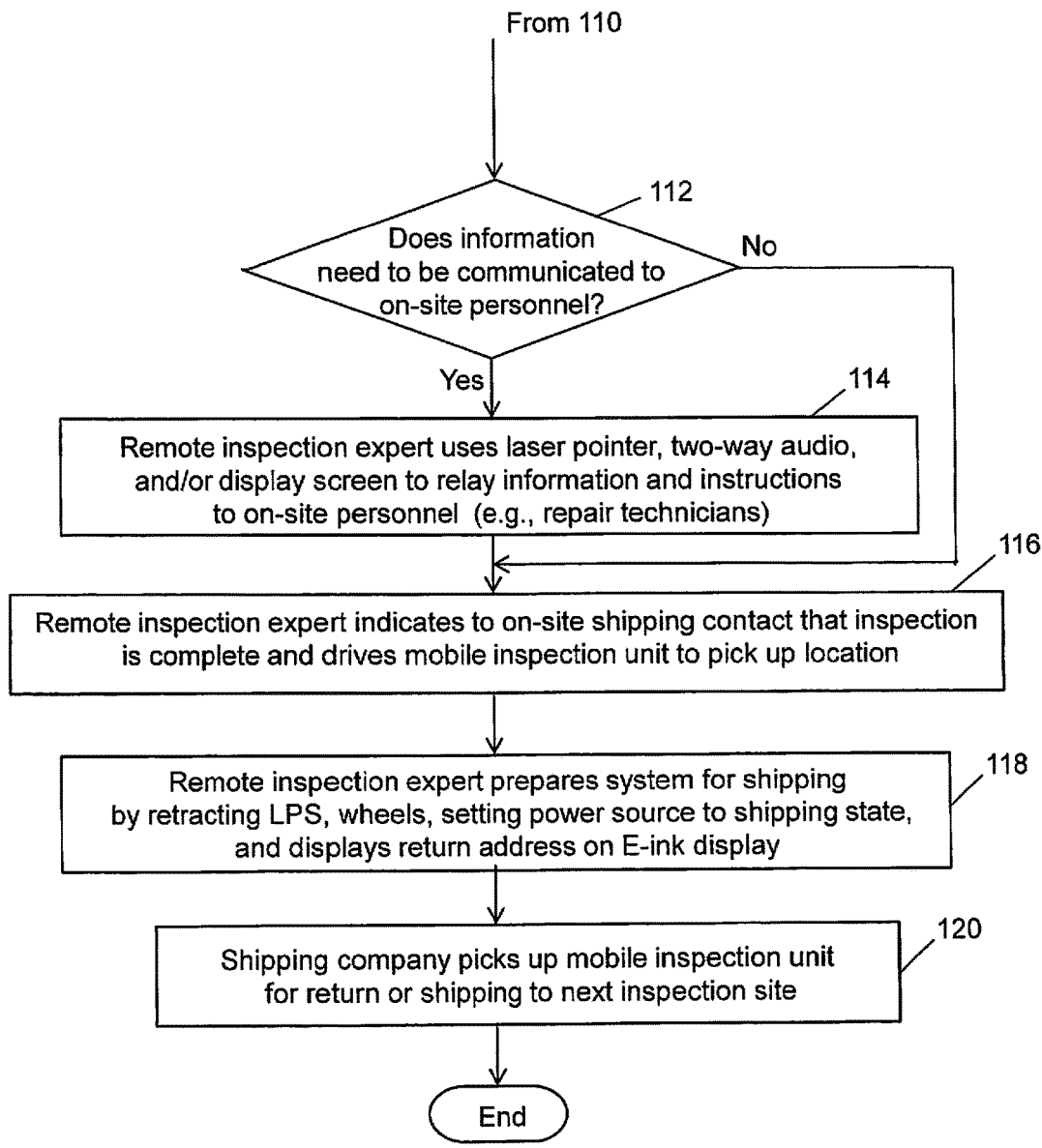
FIG. 7 is a diagram showing the mutual relationship of FIGS. 7A and 7B, which present respective portions of a flowchart showing a process for stand-off inspection of a target object at an inspection site utilizing the self-contained, remotely operable, mobile measurement system depicted in FIG. 6.

FIGS. 7A and 7B present respective portions of a flowchart showing a process for stand-off inspection of a target object at an inspection site utilizing the self-contained, remotely operable, mobile measurement system depicted in FIG. 6. In this use case, an untrained on-site person receives the inspection equipment from a shipper (step 100 in FIG. 7A). That person places the inspection equipment on the ground in the general vicinity of the target object and then notifies the remote (i.e., off-site) inspection expert (by a phone call, email, or possibly by entering a code on the mobile inspection device itself) that the system has been delivered and is in place for the inspection (steps 102). The remote inspection expert establishes a communication connection with the on-board computer of the inspection system and then runs a system diagnostic check remotely (steps 104), which may include searching for an optimal data connection. When the automated system check has been completed and a data connection established, the remote inspection expert activates the deployment actuators (step 106). The remote inspection expert then commands the mobile measurement/inspection system to move to a location of interest near the target object and stop at the desired location (step 107). With the system at the desired location, the remote inspection expert calibrates the LPS to the local coordinate system of the target object (step 108) and then begins acquiring position measurements, capturing photographs or video, etc. (steps 109). After measurement and inspection have been completed for one location on the target object, the remote inspection expert determines whether data from other locations on the target object is required (step 110). If the decision is in the affirmative, then steps 107-109 are repeated for a new location on the target object. If the decision is in the negative, then the process proceeds to step 112 (see FIG. 7B).

Referring to FIG. 7B, upon completion of the inspection the remote inspection expert determines (step 112) whether information should be communicated to on-site personnel. If information should be communicated, the remote inspection expert may use a laser pointer, two-way audio and/or display screen on the mobile measurement system to relay information and instructions to on-site personnel (e.g., repair technicians) (step 114). Thereafter the remote inspection expert indicates to the on-site shipping contact that the inspection has been completed and drives the mobile inspection unit to a pick-up location (steps 116). If a determination is made in step 112 that no information should be communicated, then steps 116 are performed without performing step 114. Then the remote inspection expert re-configures the mobile system for return shipment (steps 118), which may include retracting the LPS unit and wheels, setting the power source to a shipping state, and displaying the return shipping address on an E-ink display unit mounted to the exterior of the shipping container. The remote inspection expert then notifies the on-site personnel (or perhaps the shipping company directly) that the equipment is ready for pickup. The shipping company then picks up the mobile inspection unit for return or shipping to the next inspection site.

The mobile telepresence systems disclosed above have the ability to perform point-to-point distance measurements, as well as acquire Cartesian coordinate data defined in the coordinate system of the target object. Combining a mobile platform with real-time tracking of platform position allows the position of the LPS unit to be precisely controlled by the remote operator or by a process executed by the on-board computer. A variation of the system is ruggedized to allow for shipping to its destination without a separate shipping container; this allows the unit to be sent to the inspection site and automatically reconfigure to the mobile and inspection configurations without on-site assistance.

Additional features can be incorporated in the mobile measurement and inspection systems disclosed herein. Additional types of sensors can be deployed on the platform, such as temperature, humidity, and wind speed sensors to provide information concerning environmental conditions at the site to the remote operator. Proximity sensors can also be integrated into the mobile platform to help the system avoid collisions with objects in the environment as it moves. All terrain wheels can be used to provide additional traction in outdoor environments, or wheels that enable holonomic motion of the vehicle can be used when additional maneuverability is required. For long inspection tasks, the remote operator may ask someone at the inspection site to plug in the unit to recharge, or to swap out a replaceable power source. In the event that flexible solar panels become available, the system may be equipped with a solar recharging option. Fuel cells or even motor-generator based power sources could be used. An integrated internal heater may be added for cold environments. Additional cameras (visible light or infrared) may be included for improved situational awareness. Multiple types of networking options may be included: Wi-Fi, cell, etc. Additional sensor or actuators (e.g., grippers) could be included on the mobile platform. Remotely extendable stabilizing jacks could be added to provide more secure footing for taking measurements.

Since the concept is not limited to use in the aerospace industry, other types of manufacturing, architectural, and inspection businesses could also benefit from this technology. This capability would be particularly useful for use in areas that are not safe for humans. For example, in the event of a problem at a nuclear power plant, the ability to rapidly, safely and quantitatively measure the physical changes in the power plant structure and compare these changes to the CAD design data would be very useful.

While mobile systems have been described with reference to various embodiments, it will be understood by those skilled in the art that various changes may be made and equivalents may be substituted for elements thereof without departing from the scope of the claims. In addition, many modifications may be made to adapt a particular situation to the teachings of the invention without departing from the essential scope thereof. Therefore it is intended that the claims not be limited to the particular embodiments disclosed.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices having a processing unit (e.g., a central processing unit) and some form of memory (i.e., computer-readable medium) for storing a program which is readable by the processing unit. For example, a computer system may comprise respective processors incorporated in a plurality of devices (such as a video camera, a pan-tilt mechanism, a laser range meter, and motors) and a control computer in communication with those processors.

The method claims set forth hereinafter should not be construed to require that the steps recited therein be performed in alphabetical order (any alphabetical ordering in the claims is used solely for the purpose of referencing previously recited steps) or in the order in which they are recited. Nor should they be construed to exclude any portions of two or more steps being performed concurrently or alternatingly.

APPENDIX

Figure 8:
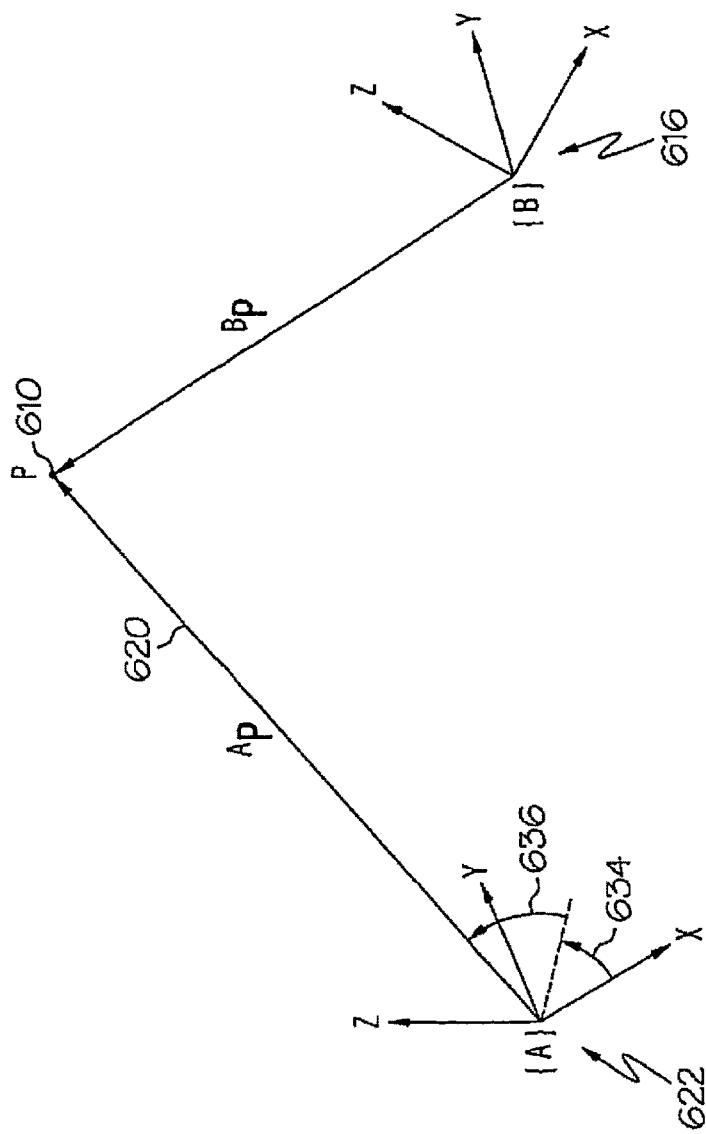
FIG. 8 is a diagram referred to in the Appendix and showing a position vector $^{A}P$ extending from the origin of an instrument coordinate system {A}, substantially along the aim point axis of the instrument, to a point of interest P and showing a position vector $^{B}P$ extending from the origin of a target object coordinate system {B} to the point of interest P.

FIG. 8 shows a position vector $^AP$ extending from the origin of an instrument coordinate system {A}, substantially along the aim point axis of the instrument, to a point of interest P and showing a position vector $^BP$ extending from the origin of a target object coordinate system {B} to the point of interest P.

Referring to FIG. 8, when the coordinates of a point P in the instrument coordinate system 622 are spherical coordinates of pan (i.e., the pan angle 634 in FIG. 8 of a vector $^AP$ to the point P), tilt (the tilt angle 638 in FIG. 8 of the vector $^AP$ to the point P), and range (the distance along the vector $^AP$ to the point P in FIG. 8), the position of the point P represented as spherical coordinates in the instrument coordinate system 622 is related to the position of the point P in X,Y,Z Cartesian coordinates in the instrument coordinate system 622 from the following equations for the forward kinematics of the instrument 618:

$$X = \text{Range} * \cos(\text{pan}) * \cos(\text{tilt})$$

$$Y = \text{Range} * \sin(\text{pan}) * \cos(\text{tilt})$$

$$Z = \text{Range} * \sin(\text{tilt})$$

where pan (azimuth) is rotation about the Z axis and tilt (elevation) is rotation about the Y axis in the instrument coordinate system 622.

It is noted that the position of the point P represented as Cartesian coordinates (X,Y,Z) in the instrument coordinate system 622 is related to the position of the point P represented as spherical coordinates (pan, tilt, range) in the instrument coordinate system 622 from the following equations for the inverse kinematics of the instrument 618:

$$\text{pan} = \tan(Y, X)^{-1}$$

$$\text{tilt} = \tan(Z, \sqrt{X^2 + Y^2})^{-1}$$

$$\text{Range} = \tan \sqrt{X^2 + Y^2 + Z^2}$$

In one implementation, a position $^BP$ (which is represented as a column vector in the form $[X,Y,Z,1]^T$) in the target object coordinate system 616 is calculated from a position $^AP$ (also a column vector in the form $[X,Y,Z,1]^T$) in the instrument coordinate system 622 from the equation:

$$^BP = {^B_AT}{^AP}$$

where T is the calibration matrix. In one example, the calibration matrix is a 4×4 homogeneous transformation matrix having the form:

$$^B_AT = \begin{bmatrix} r_{11} & r_{12} & r_{13} & X \\ r_{21} & r_{22} & r_{23} & Y \\ r_{31} & r_{32} & r_{33} & Z \\ 0 & 0 & 0 & 1 \end{bmatrix}$$

It is noted that a position $^AP$ in the instrument coordinate system 622 can be calculated from a position $^BP$ in the target object coordinate system 616 using the inverse of the calibration matrix from the equation:

$$^AP({^B_AT})^{-1}{^BP} = ({^A_BT}){^BP}$$

In one example, the three calibration points are non-collinear, and the calibration matrix is calculated as follows:

$$\vec{n}_A = V_{A12} \times V_{A13}$$

$$\vec{n}_B = \vec{V}_{B12} \times \vec{V}_{B13}$$

Figure 10:
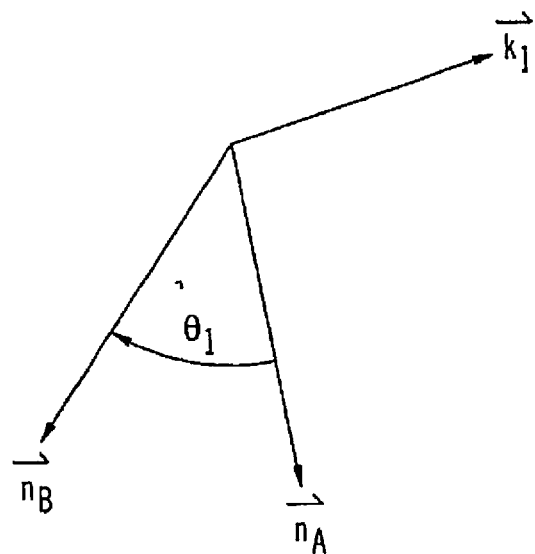
Figure 11:
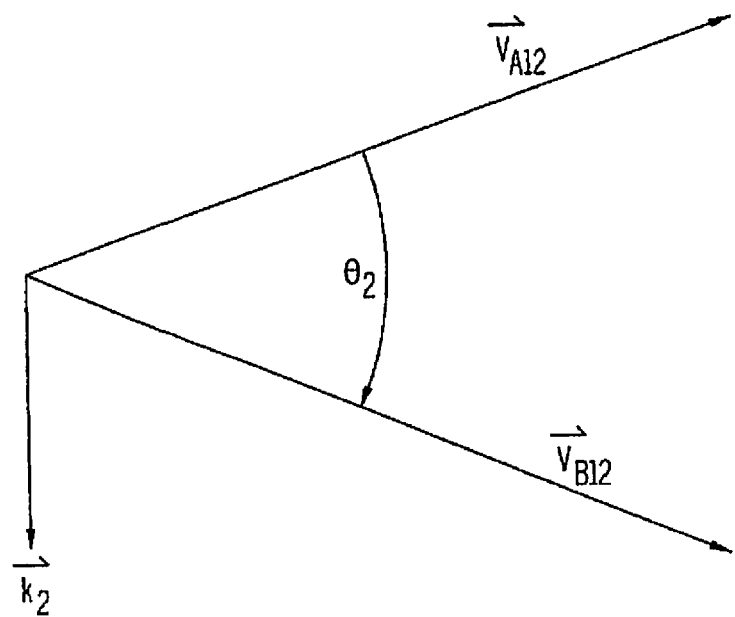

-continued $$\vec{k}_1 = \vec{n}_A \times \vec{n}_B$$

$$\theta_1 = a\cos(|\vec{n}_A| \cdot |\vec{n}_B|)$$

$$R_1 = f_1(|\vec{k}_1|, \theta_1)$$

$$\vec{k}_2 = \vec{V}_{A12} \times \vec{V}_{B12}$$

$$\theta_2 = a\cos(|\vec{V}_{A12}| \cdot |\vec{V}_{B12}|)$$

$$R_2 = f_1(|\vec{k}_2|, \theta_2)$$

$$R_{12} = R_1 R_2$$

$${}_A^B T = \left[ R_{12}, \left[ R_1 (\vec{V}_{B12} - \vec{V}_{A12}) \right]^T \right]$$

$${}_B^A T = ({}_A^B T)^{-1}$$

wherein, referring to FIGS. 9-11:

$\vec{V}_{A12}$ is the vector in coordinate system A that extends from point $P_{A1}$ to $P_{A2}$;

$\vec{V}_{A13}$ is the vector in coordinate system A that extends from point $P_{A1}$ to $P_{A3}$;

$\vec{V}_{B12}$ is the vector in coordinate system A that extends from point $P_{B1}$ to $P_{B2}$;

$\vec{V}_{B13}$ is the vector in coordinate system A that extends from point $P_{B1}$ to $P_{B3}$;

$\vec{n}_A$ and $\vec{n}_B$ are the normals created from the vector cross products;

$\vec{K}_1$ and $\vec{K}_2$ are axes of rotation;

$\theta_1$ and $\theta_2$ are rotation angles about axes $\vec{K}_1$ and $\vec{K}_2$, respectively;

$R_1$, $R_2$, and $R_{12}$ are 3×3 symmetric rotation matrices; and $f_1(\ )$ is the function (known to those skilled in the art and described, for example, in "Introduction to Robotics: Mechanics and Control", 3rd edition, by John J. Craig and published July 2004 by Prentice Hall Professional Technical Reference) which generates a 3×3 rotation matrix from the angle-axis definition described below:

$$f_1(\hat{k}, \theta) = \begin{bmatrix} k_x k_x v\theta + c\theta & k_x k_y v\theta - k_z s\theta & k_x k_z v\theta + k_y s\theta \\ k_x k_y v\theta + k_z s\theta & k_y k_y v\theta + c\theta & k_y k_z v\theta - k_x s\theta \\ k_x k_z v\theta - k_y s\theta & k_y k_z v\theta + k_x s\theta & k_z k_z v\theta + c\theta \end{bmatrix}$$

where $c\theta = \cos(\theta)$, $s\theta = \sin(\theta)$, $v\theta = 1 - \cos(\theta)$, and $\hat{k} = [k_x, k_y, k_z]$.

Note that the 4×4 homogeneous calibration matrix ${}_A^B T$ only is computed once for any position of the pointing instrument relative to the target object, and ${}_A^B T$ can then be used to convert any number of vectors from coordinate system A (the instrument coordinate system 622) into coordinate system B (the target object coordinate system 616). It is also noted that the inverse calibration matrix ${}_B^A T$ can be calculated by calculating the inverse of the calibration matrix ${}_A^B T$ or can be calculated directly by switching the order of the vectors in the first equations of the previous paragraph.

The invention claimed is:

1. A method for teleoperation of a self-powered mobile platform from a command workstation, comprising:
   (a) mounting a local positioning system and a computer onboard the mobile platform;
   (b) establishing a communication channel between the computer onboard the mobile platform and the command workstation via a wireless connection;
   (c) via the wireless connection, remotely controlling the mobile platform to move to a first location near the target object;
   (d) via the wireless connection and while the mobile platform is at said first location, remotely activating the local positioning system to generate a calibration transformation matrix representing the current position and orientation of the local positioning system relative to a coordinate system of a target object; and
   (e) via the wireless connection and while the mobile platform is at said first location, remotely activating the mobile platform to move to a second location which is calculated based at least in part on the calibration transformation matrix.

2. The method as recited in claim 1, wherein said second location of the mobile platform is calculated based at least in part also on a calibration transformation matrix representing a previous position and orientation of the local positioning system relative to a coordinate system of a target object.

3. The method as recited in claim 1, further comprising:
   via the wireless connection and while the mobile platform is at said first location, remotely activating the local positioning system to calculate a position of a point of interest on the target object relative to the coordinate system of a target object,
   wherein said second location of the mobile platform is calculated based at least in part also on said calculated position of the point of interest.

4. The method as recited in claim 3, further comprising:
   mounting a stand-off non-destructive inspection unit onboard the mobile platform such that a laser source of the local positioning system and the stand-off non-destructive inspection unit have a fixed positional relationship; and
   via the wireless connection and while the mobile platform is at said second location, remotely activating the stand-off non-destructive inspection unit to acquire inspection data from a surface area of the target object without contacting that surface area.

5. A portable measurement system comprising:
   a shipping container;
   a multiplicity of wheels mechanically coupled to said shipping container for movement between respective retracted positions inside said shipping container in a shipping configuration and respective extended positions outside said shipping container in a mobile platform configuration;
   a local positioning system unit mechanically coupled to said shipping container for movement between a retracted positions inside said shipping container in said shipping configuration and an extended position outside said shipping container in said mobile platform configuration, said local positioning system comprising wave energy projecting means for projecting wave energy in a direction, directional control means for orienting said wave energy projecting means to project in a direction having a selected pan angle and a selected tilt angle; and means for detecting wave energy returned from a target object after each projection of wave energy;
   a computer disposed inside said shipping container,
   a wireless adapter electrically coupled to said computer and capable of receiving commands from an in-range wireless network access point and transmitting said commands to said computer;

a drivetrain disposed inside said shipping container for driving at least one of said wheels to rotate; and at least one deployment actuator disposed inside said shipping container for actuating movement of said multiplicity of wheels between said retracted and extended positions of said wheels and movement of said local positioning system between said retracted and extended positions of said local positioning system, wherein said computer is configured to perform the following operations:

controlling said at least one actuator in response to a deployment command received via said wireless adapter;

controlling said drive train to move said mobile platform to a location near a target object in accordance with a platform location command received via said wireless adapter; and controlling said local positioning system to calibrate its position and orientation relative to a coordinate system of a target object in response to a calibration command received via said wireless adapter.

6. The system as recited in claim 1, wherein said at least one actuator comprises a rotary actuator for extending and retracting said wheels by rotation.

7. The system as recited in claim 6, further comprising a multiplicity of pivotable arms coupled to said rotary actuator, wherein each of said wheels is rotatably coupled to an end of a respective one of said multiplicity of arms, and said rotary actuator comprises an electric motor and a plurality of gears which couple said pivotable arms to said electric motor.

8. The system as recited in claim 1, wherein said at least one actuator comprises a linear actuator for extending and retracting said local positioning system by translation.

9. The system as recited in claim 8, wherein said linear actuator comprising an electric motor and a lead screw which couples said local positioning system to said electric motor.

10. The system as recited in claim 1, further comprising a stand-off nondestructive inspection sensor affixed to said local positioning system.

11. The system as recited in claim 10, wherein said stand-off nondestructive inspection sensor employs one of the following inspection techniques: near-infrared spectroscopy, terahertz imaging, microwave imaging, x-ray backscatter imaging, infrared thermography, laser shearography, laser ultrasonic testing and laser vibrometry.

12. A mobile non-destructive inspection system comprising:

a shipping container;

a multiplicity of wheels mechanically coupled to said shipping container for movement between respective retracted positions inside said shipping container in a shipping configuration and respective extended positions outside said shipping container in a mobile platform configuration;

a pan-tilt mechanism mechanically coupled to said shipping container for movement between a retracted positions inside said shipping container in said shipping configuration and an extended position outside said shipping container in said mobile platform configuration;

an assembly comprising a stand-off nondestructive inspection unit and a local positioning system, said assembly being mounted to said pan-tilt mechanism;

a computer disposed inside said shipping container, a wireless adapter electrically coupled to said computer and capable of receiving commands from an in-range wireless network access point and transmitting said commands to said computer;

a drivetrain disposed inside said shipping container for driving at least one of said wheels to rotate;

at least one deployment actuator disposed inside said shipping container for actuating movement of said multiplicity of wheels between said retracted and extended positions of said wheels and movement of said assembly between said retracted and extended positions of said local positioning system, wherein said computer is configured to perform the following operations:

controlling said at least one actuator in response to a deployment command received via said wireless adapter;

controlling said drive train to move said mobile platform to a location near a target object in accordance with motion commands received via said wireless adapter;

controlling said local positioning system to calibrate its position and orientation relative to a coordinate system of a target object in response to a calibration command received via said wireless adapter; and controlling said stand-off nondestructive inspection unit to acquire inspection data from the target object in response to an inspection command received via said wireless adapter.

13. The system as recited in claim 12, wherein said stand-off nondestructive inspection sensor employs one of the following inspection techniques: near-infrared spectroscopy, terahertz imaging, microwave imaging, x-ray backscatter imaging, infrared thermography, laser shearography, laser ultrasonic testing and laser vibrometry.

14. The system as recited in claim 12, wherein said at least one actuator comprises a rotary actuator for extending and retracting said wheels by rotation.

15. The system as recited in claim 14, further comprising a multiplicity of pivotable arms coupled to said rotary actuator, wherein each of said wheels is rotatably coupled to an end of a respective one of said multiplicity of arms, and said rotary actuator comprises an electric motor and a plurality of gears which couple said pivotable arms to said electric motor.

16. The system as recited in claim 12, wherein said at least one actuator comprises a linear actuator for extending and retracting said local positioning system by translation.

17. The system as recited in claim 16, wherein said linear actuator comprising an electric motor and a lead screw which couples said local positioning system to said electric motor.

18. A method for teleoperation of a self-powered mobile stand-off non-destructive inspection system from a command workstation, comprising:

(a) configuring the self-powered mobile stand-off non-destructive inspection system so that a multiplicity of wheels, a local positioning system and a nondestructive inspection sensor are contained inside a shipping container in a shipping configuration along with a computer;

(b) placing the shipping container in the shipping configuration at a remote inspection site where a target object is located;

(c) establishing a communication channel between the computer inside the shipping container and the command workstation via a wireless connection; and (d) via the wireless connection, remotely activating a transformation of the self-powered mobile stand-off non-destructive inspection system from the shipping configuration to a deployed configuration in which the wheels, local positioning system and stand-off nondestructive inspection unit are extended outside the shipping container.

19. The method as recited in claim 18, further comprising:
(e) via the wireless connection, remotely controlling the deployed stand-off non-destructive inspection system to move to a location near the target object;
(f) via the wireless connection and while the stand-off non-destructive inspection system is at said location, remotely activating the local positioning system to calibrate its position and orientation relative to a coordinate system of a target object; and
(g) via the wireless connection and while the stand-off non-destructive inspection system is at said location, remotely activating the stand-off non-destructive inspection system to acquire inspection data from a surface area of the target object without contacting that surface area while the stand-off non-destructive inspection system is at said location by sending an inspection command from the command workstation to the computer via the communication channel.

20. The method as recited in claim 18, wherein the wheels are extended by rotation and the local positioning system and stand-off nondestructive inspection unit are extended by translation.

\* \* \* \* \*